(12) United States Patent
Bor et al.

(10) Patent No.: US 12,208,036 B2
(45) Date of Patent: Jan. 28, 2025

(54) SURGICAL LASER SYSTEM WITH ILLUMINATION

(71) Applicant: Alcon Inc., Fribourg (CH)

(72) Inventors: Zsolt Bor, San Clemente, CA (US); Adela Apostol, Laguna Hills, CA (US); Daniel Castro, Lake Forest, CA (US); Reza Khazaeinezhad, Lake Forest, CA (US); Mikhail Ovchinnikov, Dana Point, CA (US); Alireza Malek Tabrizi, Irvine, CA (US); Keith Watanabe, Irvine, CA (US); Corey Stewart, Irvine, CA (US)

(73) Assignee: Alcon Inc., Fribourg (CH)

( * ) Notice: Subject to any disclaimer, the term of this patent is extended or adjusted under 35 U.S.C. 154(b) by 373 days.

(21) Appl. No.: 17/662,148

(22) Filed: May 5, 2022

(65) Prior Publication Data

US 2022/0354692 A1  Nov. 10, 2022

Related U.S. Application Data

(60) Provisional application No. 63/185,623, filed on May 7, 2021.

(51) Int. Cl.
A61F 9/008 (2006.01)
(52) U.S. Cl.
CPC .... *A61F 9/008* (2013.01); *A61F 2009/00887* (2013.01)
(58) Field of Classification Search
CPC ....................................................... A61F 9/008

USPC ............................................................ 606/6
See application file for complete search history.

(56) References Cited

U.S. PATENT DOCUMENTS

| 5,921,981 | A | 7/1999 | Bahmanyar et al. |
|---|---|---|---|
| 8,267,925 | B2 | 9/2012 | Raksi |
| 8,371,694 | B2 | 2/2013 | Artsyukhovich |
| 8,398,240 | B2 | 3/2013 | Smith |
| 9,055,885 | B2 | 6/2015 | Horvath |
| 9,827,144 | B2 | 11/2017 | Abraham |
| 10,070,988 | B2 | 9/2018 | Mcdonell |
| 10,537,401 | B2 | 1/2020 | Dos Santos |
| 11,109,938 | B2 | 9/2021 | Horn et al. |
| 11,331,219 | B2 | 5/2022 | Farley |
| 11,771,597 | B2 | 10/2023 | Bacher |
| 2005/0267551 | A1* | 12/2005 | Bhullar ................ A61N 5/0624 607/88 |
| 2009/0067189 | A1 | 3/2009 | Boutoussov et al. |
| 2018/0360657 | A1 | 12/2018 | Bor et al. |
| 2019/0175300 | A1 | 6/2019 | Horn et al. |
| 2019/0201238 | A1 | 7/2019 | Bacher et al. |

(Continued)

FOREIGN PATENT DOCUMENTS

WO    0044294 A1    8/2000

*Primary Examiner* — Nadia A Mahmood

(57) ABSTRACT

Systems and methods are disclosed for a surgical laser system with illumination. In some embodiments, a laser system comprises a surgical laser and an illumination source having their outputs combined into a fiber-optic cable and directed by the fiber-optic cable to a target surface. The illuminating visible light may be continuous and/or in pulses. Surgical laser pulses and illumination pulses may be synchronized for a stroboscopic effect. The laser system may also monitor laser electromagnetic radiation that is returned back through the fiber-optic cable.

18 Claims, 4 Drawing Sheets

(56) References Cited

U.S. PATENT DOCUMENTS

| | | |
|---|---|---|
| 2020/0107960 A1 | 4/2020 | Bacher et al. |
| 2021/0290438 A1 | 9/2021 | Hallen |
| 2022/0110793 A1 | 4/2022 | Sawicz et al. |

\* cited by examiner

SURGICAL LASER SYSTEM WITH ILLUMINATION

TECHNICAL FIELD

The present disclosure is directed laser systems, such as laser systems used in ophthalmic procedures.

BACKGROUND

Lasers are used in many different medical procedures including a number of different ophthalmic procedures. For example, lasers may be used in cataract surgery, such as for fragmenting the cataractous lens. In some procedures, a laser is used for initial fragmentation of the lens, followed by phacoemulsification of the lens by an ultrasonic handpiece to complete the breakdown of the lens for removal. In other procedures, the laser may be used for complete fragmentation or phacoemulsification of the lens for removal, without the need for a separate application of ultrasonic energy. Lasers may also be used for other steps in cataract surgery, such as for making the corneal incision(s) and/or opening the capsule.

Lasers may also be used in vitreoretinal surgery. In some procedures, a laser may be used for vitrectomy, to sever or break the vitreous fibers for removal. The laser may be incorporated into a vitrectomy probe, and the energy from the laser may be applied to the vitreous fibers to sever or break the vitreous fibers for removal.

In other vitreoretinal applications, lasers may be used for photocoagulation of retinal tissue. Laser photocoagulation may be used to treat issues such as retinal tears and/or the effects of diabetic retinopathy.

Other surgical laser uses include brain surgery, neurosurgery, otolaryngology, vascular surgery, dental surgery, cosmetic surgery, and many others.

U.S. Patent Application Publication No. 2018/0360657 discloses examples of an ophthalmic laser system. That application describes laser uses such as for forming surgical cuts or for photodisrupting ophthalmic tissue as well as for cataract surgery, such as laser-assisted cataract surgery (LACS). U.S. Patent Application Publication No. 2019/0201238 discloses other examples of an ophthalmic laser system. That application describes laser uses such as in a vitrectomy probe for severing or breaking vitreous fibers. U.S. Patent Application Publication No. 2018/0360657 and U.S. Patent Application Publication No. 2019/0201238 are expressly incorporated by reference herein in their entirety.

There is a need for improved laser systems and associated methods.

SUMMARY

The present disclosure is directed to improved laser systems and methods for operating laser systems with illumination.

In some embodiments, a laser system comprises a surgical laser configured to emit electromagnetic radiation, an illumination source configured to emit illuminating visible light, and at least one fiber-optic cable for transmitting the surgical laser electromagnetic radiation and the illuminating visible light. The at least one fiber-optic cable is configured to receive the electromagnetic radiation from the surgical laser and the illuminating visible light from the illumination source at the proximal end of the at least one fiber-optic cable and to transmit the electromagnetic radiation from the surgical laser and the illuminating visible light from the illumination source to the distal end of the at least one fiber-optic cable and out of the distal end of at least one the fiber-optic cable to a target surface.

The illumination source may be configured to emit the illuminating visible light continuously for a desired period of time and/or to emit the illuminating visible light in pulses. The surgical laser may be configured to emit the electromagnetic radiation from the surgical laser in pulses, and the laser system may be configured to synchronize pulses from the surgical laser and pulses from the illumination source to create a stroboscopic effect.

The fiber-optic cable may have at least one optical fiber configured to receive the electromagnetic radiation from the surgical laser and the illuminating visible light from the illumination source. Additionally or alternatively, the fiber-optic cable may have at least a first optical fiber configured to receive the electromagnetic radiation from the surgical laser and at least a second optical fiber configured to receive the illuminating visible light from the illumination source.

The at least one fiber-optic cable may comprise a delivery fiber-optic cable and an output fiber-optic cable each having a proximal end and a distal end. The output fiber-optic cable may be positioned distal to the delivery fiber-optic cable, and the proximal end of the output fiber-optic cable may be configured to receive the electromagnetic radiation from the surgical laser and the illuminating visible light from the illumination source from the distal end of the delivery fiber-optic cable.

The laser system may comprise a laser housing. The surgical laser may be located inside the laser housing. The illumination source may also be located inside the laser housing. At least one fiber-optic cable may be adapted to be removably connected to the laser housing.

The laser system may further comprise a monitoring sensor positioned to detect returned laser electromagnetic radiation.

In some embodiments, a method of operating a laser system comprises emitting electromagnetic radiation from a surgical laser, emitting illuminating visible light from an illumination source, receiving the electromagnetic radiation from the surgical laser and the illuminating visible light from the illumination source at a proximal end of at least one fiber-optic cable, and transmitting the electromagnetic radiation from the surgical laser and the illuminating visible light through the at least one fiber-optic cable to a distal end of the at least one fiber-optic cable and out of the distal end of the at least one fiber-optic cable to a target surface.

The step of emitting illuminating visible light from the illumination source to the at least one fiber-optic cable may comprise emitting the illuminating visible light from the illumination source continuously for a desired period of time. The step of emitting illuminating visible light from the illumination source to the at least one fiber-optic cable may comprise emitting the illuminating visible light from the illumination source in pulses. The step of emitting electromagnetic radiation from a surgical laser to at least one fiber-optic cable may comprise emitting the electromagnetic radiation from the surgical laser in pulses, the step of emitting illuminating visible light from the illumination source to the at least one fiber-optic cable may comprise emitting the illuminating visible light from the illumination source in pulses, and the laser system may synchronize the pulses from the surgical laser and the pulses from the illumination source to create a stroboscopic effect. The stroboscopic effect may be, for example, a slow-motion effect.

Further examples and features of embodiments of the invention will be evident from the drawings and detailed description.

BRIEF DESCRIPTION OF THE DRAWINGS

The accompanying drawings illustrate example implementations of the devices and methods disclosed herein and, together with the description, serve to explain the principles of the present disclosure.

Figure 1:
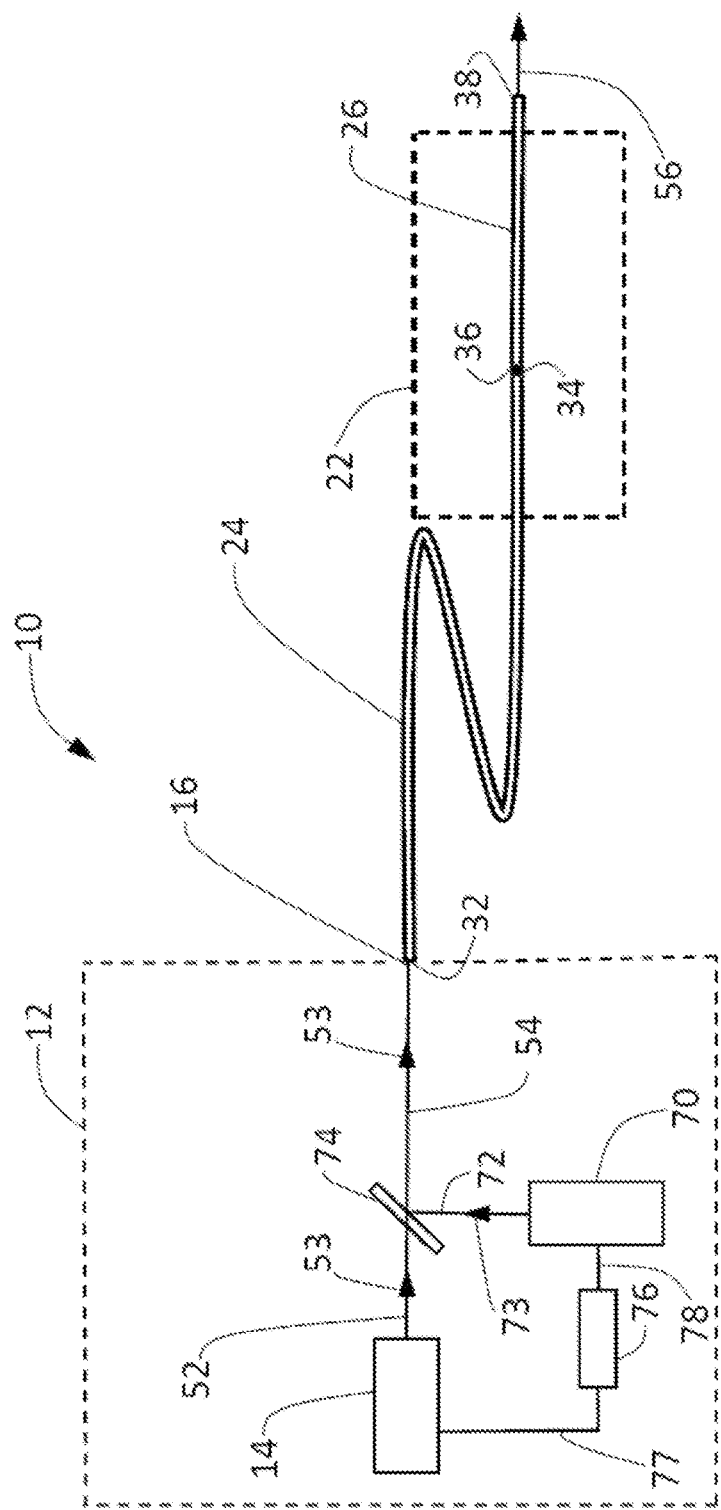
FIG. 1 shows a schematic diagram of an example laser system configured for delivering electromagnetic radiation from a surgical laser and illuminating visible light from an illumination source in accordance with the disclosure.

The accompanying drawings may be better understood by reference to the following detailed description.

DETAILED DESCRIPTION

For the purposes of promoting an understanding of the principles of the disclosure, reference will now be made to the implementations illustrated in the drawings, and specific language will be used to describe those implementations and other implementations. It will nevertheless be understood that no limitation of the scope of the claims is intended by the examples shown in the drawings or described herein. Any alterations and further modifications to the illustrated or described systems, devices, instruments, or methods, and any further application of the principles of the present disclosure, are fully contemplated as would normally occur to one skilled in the art to which the disclosure relates. In particular, the features, components, and/or steps described with respect to one implementation of the disclosure may be combined with features, components, and/or steps described with respect to other implementations of the disclosure. For simplicity, in some instances the same reference numbers are used throughout the drawings to refer to the same or like parts.

The terms "proximal" and "distal" are used herein to designate directions or ends of components, wherein the proximal direction or end is directed or oriented toward the laser source and the distal direction or end is directed or oriented toward the working output end, such as the working output end or tip of a fiber-optic cable adjacent to tissue to be treated. The designations "first" and "second" as used herein are not meant to indicate or imply any particular positioning or other characteristic. Rather, when the designations "first" and "second" are used herein, they are used only to distinguish one component from another. For example, unless otherwise specified, a first fiber-optic cable or a second fiber-optic cable may be positioned closer to the laser source.

FIG. 1 shows a schematic diagram of an example laser system 10 configured for delivering electromagnetic radiation from a surgical laser and illuminating visible light from an illumination source in accordance with the disclosure. The laser system 10 may be a laser system suitable for one or more ophthalmic procedures. The laser system 10 may be a stand-alone laser system or may be a laser module in an ophthalmic system or console used for ophthalmic procedures.

In some embodiments, the laser system 10 may be suitable for cataract surgery. In some embodiments, the output energy of the laser system is suitable for fragmentation or phacoemulsification a cataractous lens. In some examples, the laser output is used for initial fragmentation of the cataractous lens, followed by phacoemulsification of the lens using an ultrasonic handpiece to complete the breakdown of the lens for removal. In other examples, the laser output is used for fragmentation or phacoemulsification of the lens to a sufficient degree for removal of the lens without the need for a separate application of ultrasonic energy. Additionally or alternatively, the laser output may be suitable for making corneal incisions and/or for opening the lens capsule.

In other embodiments, the laser system may be suitable for vitreoretinal surgery. In some embodiments, the output energy of the laser system is suitable for severing or breaking vitreous fibers for removal. In other vitreoretinal applications, the laser output may be suitable for ophthalmic tissue treatment, such as photocoagulation of retinal tissue to treat issues such as retinal tears and/or the effects of diabetic retinopathy.

As shown in FIG. 1, the laser system 10 includes a laser housing 12, shown schematically as a dashed-line box in FIG. 1. The laser housing 12 houses a surgical laser 14. In addition to the surgical laser 14, other components may be located in the laser housing 12. For example, the laser housing 12 may house components for operating the surgical laser 14. In addition, the laser housing 12 may house components in the optical path of the laser output, such as one or more lenses or other optical components (not shown).

The surgical laser 14 may be any type of laser suitable for the desired application. The surgical laser 14 may output suitable electromagnetic radiation at any suitable wavelength. For example, the surgical laser 14 may emit electromagnetic radiation in one or more wavelengths in the visible, infrared, and/or ultraviolet wavelengths. The surgical laser 14 may operate or be operated to emit a continuous beam of electromagnetic radiation. Alternatively, the surgical laser 14 may operate or be operated to emit a pulsed beam.

In one example, the surgical laser 14 operates in the infrared range. For example, the surgical laser 14 may output electromagnetic radiation in the mid-infrared range, for example in a range of about 2.0 microns to about 4.0 microns. Some example wavelengths include about 2.5 microns to 3.5 microns, such as about 2.775 microns, about 2.8 microns, or about 3.0 microns. Such a surgical laser may be suitable, for example, for lens fragmentation in cataract surgery, or for other procedures.

In another example, the surgical laser 14 emits electromagnetic radiation in the ultraviolet range. In another example, the surgical laser 14 emits electromagnetic radiation in the visible range.

The laser system 10 is designed to direct the laser electromagnetic radiation from the surgical laser 14 to an output port 16 of the laser housing 12. In FIG. 1, the output port 16 is indicated schematically as the distal end of the optical path 54 in the laser housing 12, although it will be understood that an optical component, such as a lens, may be located at the output port 16. The laser system 10 may direct the laser electromagnetic radiation from the surgical laser 14 to the output port 16 through one or more optical components.

An instrument 22 may be optically connected to the laser housing 12 to receive the laser electromagnetic radiation from the output port 16. The instrument 22 may be, for example, a handpiece for an ophthalmic procedure. The instrument or handpiece 22 is shown schematically as a dashed-line box in FIG. 1.

The instrument or handpiece 22 may be connected to the laser housing 12 by at least one fiber-optic cable, such as a delivery fiber-optic cable 24. The delivery fiber-optic cable 24 may be flexible and relatively long to give the operator flexibility in maneuvering the handpiece 22 at some distance away from the laser housing 12. The delivery fiber-optic cable 24 may be, for example, 1 to 3 meters in length. In an example embodiment, the delivery fiber-optic cable 24 may be about 2 meters in length.

The delivery fiber-optic cable 24 may be a part of the handpiece 22, permanently attached thereto. Alternatively, the delivery fiber-optic cable 24 may be removably connected to the handpiece 22. The delivery fiber-optic cable 24 may be permanently or removably connected to the handpiece 22 either directly or through one or more other components, including through one or more other fiber-optic cables.

At its proximal end 32, the delivery fiber-optic cable 24 may be removably connected to the laser housing 12. The delivery fiber-optic cable 24 may have a connector (not shown) that mates with a connector at the output port 16 of the laser housing 12. Alternatively, the delivery fiber-optic cable 24 may be permanently attached to the laser housing 12. The delivery fiber-optic cable 24 may be permanently or removably connected to the laser housing 12 either directly or through one or more other components, including through one or more other fiber-optic cables.

At the distal end 34 of the delivery fiber-optic cable 24, the delivery fiber-optic cable 24 may be optically coupled to an output fiber-optic cable 26. The output fiber-optic cable 26 has a proximal end 36 and a distal end 38. The distal end output 38 of the output fiber-optic cable 26 constitutes the distal end output of the laser system 10. At its proximal end 36, the output fiber-optic cable 26 may be joined to a connector or ferrule that joins the output fiber-optic cable 26 to the handpiece 22, such that the output fiber-optic cable 26 constitutes a removable part of the handpiece 22. In other embodiments, the output fiber-optic cable may be permanently attached to the rest of the handpiece 22. The output fiber-optic cable 26 may be permanently or removably connected to the rest of the handpiece 22 either directly or through one or more other components. The distal end 34 of the delivery fiber-optic cable 24 may be optically coupled to the proximal end 36 of the output fiber-optic cable 26 either directly or through one or more other components. For example, one or more fiber-optic cables may be positioned between the delivery fiber-optic cable 24 and the output fiber-optic cable 26. One or more other components, such as connectors, lenses, or other components may be positioned between the delivery fiber-optic cable 24 and the output fiber-optic cable 26.

The output fiber-optic cable 26 may be any suitable length. For example, the output fiber-optic cable 26 may be between 20 mm and 100 mm in length. In an example embodiment, the output fiber-optic cable 26 may be about 50 mm in length.

In one example embodiment, the output fiber-optic cable 26 is fixed to a connector or ferrule that can be joined to and removed from the rest of the handpiece 22. The output fiber-optic cable 26 may be a disposable component, such that after use the output fiber-optic cable 26 may be removed from the rest of the handpiece 22 and discarded. A new disposable output fiber-optic cable 26 may be joined to the rest of the handpiece 22 for a subsequent procedure.

The fiber-optic cables in the laser system may have one or more optical fibers capable of transmitting electromagnetic radiation suitable for the intended application. Any suitable material fiber may be used, including glass fibers or plastic fibers. In one example embodiment, the delivery fiber-optic cable 24 may include one or more germanium oxide (GeO2) fibers, and the output fiber-optic cable 26 may include one or more sapphire fibers. Many other examples are possible.

In the embodiment of FIG. 1, in addition to the surgical laser 14 configured to emit electromagnetic radiation, the laser system 10 also comprises an illumination source 70 configured to emit illuminating visible light. The proximal end 32 of the delivery fiber-optic cable 24 is configured to receive the electromagnetic radiation from the surgical laser 14 and the illuminating visible light from the illumination source 70. The delivery fiber-optic cable 24 is configured to transmit the electromagnetic radiation from the surgical laser 14 and the illuminating visible light from the illumination source 70 from the proximal end 32 of the delivery fiber-optic cable 24 to the distal end 34 of the delivery fiber-optic cable 24 and out of the distal end 34 of the delivery fiber-optic cable 24. The proximal end 36 of the output fiber-optic cable 26 is configured to receive the electromagnetic radiation from the surgical laser and the illuminating visible light from the illumination source from the distal end 34 of the delivery fiber-optic cable 24. The output fiber-optic cable 26 is configured to transmit the electromagnetic radiation from the surgical laser 14 and the illuminating visible light from the illumination source 70 from the proximal end 36 of the output fiber-optic cable 26 to the distal end 38 of the output fiber-optic cable 26 and out of the distal end 38 of the output fiber-optic cable 26 to a target surface, such as ophthalmic tissue or other tissue.

The illumination provided through the fiber-optic cable illuminates the area of the surgical laser target. The illumination can help the operator visualize the target location and the surgical process.

In the example of FIG. 1, the electromagnetic radiation from the surgical laser 14 and the illuminating visible light from the illumination source 70 are combined in the laser housing 12 to travel along a common optical path 54 to the output 16 of the laser housing 12. The combining may be accomplished through one or more suitable optical components. For example, in the embodiment of FIG. 1, the laser system 10 includes a beam combining component 74 configured to combine the electromagnetic radiation from the surgical laser 14 and the illuminating visible light from the illumination source 70. The beam combining component 74 may be, for example, a beam splitter, dichroic mirror, polarizing beam splitter, dispersive prism, diffraction grating, or other suitable beam combining component.

In the illustrated example, the surgical laser 14 emits electromagnetic radiation along optical path 52 in the direction of arrow 53, and the beam combining component 74 permits the electromagnetic radiation from the surgical laser 14 to pass through the beam combining component 74 to travel along optical path 54 to the output 16 and the delivery fiber-optic cable 24. The illumination source 70 emits illuminating visible light along optical path 72 in the direction of arrow 73, and the beam combining component 74 reflects that illuminating visible light and directs it to travel along optical path 54 to the output 16 and the delivery fiber-optic cable 24.

In an alternative example, the surgical laser 14 is in the position of the illumination source 70 in FIG. 1, and the illumination source 70 is in the position of the surgical laser 14 in FIG. 1. In this example, the illumination source 70 emits illuminating visible light along optical path 52 in the direction of arrow 53, and the beam combining component 74 permits the illuminating visible light from the illumination source 70 to pass through the beam combining component 74 to travel along optical path 54 to the output 16 and the delivery fiber-optic cable 24. The surgical laser 14 emits electromagnetic radiation along optical path 72 in the direction of arrow 73, and the beam combining component 74 reflects that electromagnetic radiation from the surgical laser 14 and directs it to travel along optical path 54 to the output 16 and the delivery fiber-optic cable 24.

The delivery fiber-optic cable 24 and the output fiber-optic cable 26 may each have one or more optical fibers capable of transmitting the surgical laser electromagnetic radiation and/or the illuminating visible light. In some embodiments, the electromagnetic radiation from the surgical laser and the illuminating visible light from the illumination source are received by and transmitted through the same optical fiber(s) within one or more of the fiber-optic cables. In other embodiments, the electromagnetic radiation from the surgical laser is received by and transmitted through one or more first optical fiber(s) within a fiber-optic cable, and the illuminating visible light from the illumination source is received by and transmitted through one or more second optical fiber(s) within the fiber-optic cable. For example, the electromagnetic radiation from the surgical laser may be directed to a first output of the laser housing, while the illuminating visible light from the illumination source is directed to a second output of the laser housing. The delivery fiber-optic cable may have a bifurcated input for connecting to both outputs, with one or more first optical fiber(s) connecting to the first output to receive the electromagnetic radiation from the surgical laser, and one or more second optical fiber(s) connecting to the second output to receive the illuminating visible light from the illumination source. The two branches may be brought together into a single fiber-optic cable, with both the first optical fiber(s) and the second optical fiber(s) within the fiber-optic cable.

The illumination source 70 may emit the illuminating visible light continuously or in pulses. For example, in some embodiments, the illumination source 70 may emit the illuminating visible light continuously when it is in operation. The operator may have control over turning the illumination source 70 on or off, such that the continuous illuminating visible light can be emitted for a desired period of time. In other embodiments, the illumination source 70 may emit the illuminating visible light in pulses when it is in operation. The operator may have control over turning the illumination source 70 on or off, such that the pulsed illuminating visible light can be emitted for a desired period of time. In other embodiments, the illumination source 70 may be capable of emitting the illuminating visible light either continuously or in pulses, depending upon a selected mode of operation. The operator may have control over turning the illumination source 70 on or off and of selecting the operating mode and switching between operating modes, such that the illuminating visible light can be emitted continuously or in pulses and switched between emitting continuous illuminating visible light and pulsed illuminating visible light.

In some embodiments, the surgical laser 14 is configured to emit the electromagnetic radiation in pulses, the illumination source 70 is configured to emit the illuminating visible light in pulses, and the laser system is configured to synchronize the pulses from the surgical laser 14 and the pulses from the illumination source 70 to create a stroboscopic effect. The laser system 10 may include a trigger 76 for coordinating the pulses. The trigger 76 may receive input from the surgical laser 14 along communication connection 77 and send signals regarding the pulses of the surgical laser 14 to the illumination source 70 along communication connection 78. Additionally or alternatively, the trigger 76 may receive input from the illumination source 70 along communication connection 78 and send signals regarding the pulses of the illumination source 70 to the surgical laser 14 along communication connection 78. For example, the timing of the pulses of the surgical laser 14 may be used to trigger the timing of the pulses of the illumination source 70. Similarly, the timing of the pulses of the illumination source 70 may be used to trigger the timing of the pulses of the surgical laser 14.

The laser system 10 creates a stroboscopic effect by operating the surgical laser 14 and the illumination source 70 in pulses at selected frequency rates depending on the effect desired. For example, if the surgical laser 14 is operated with a pulse frequency of 1 kHz and the illumination source 70 is synchronized to the surgical laser 14 but operated with a pulse frequency of 999 Hz, the result is a stroboscopic effect showing the process slowed down 1000 times.

Other stroboscopic effects can be achieved with other synchronizations. For example, if the frequency of the illumination source 70 is set at the same frequency as the surgical laser 14, the motion at the surgical tip may appear stopped or paused. A slow-motion effect can be achieved by a frequency of the illumination source 70 that is close to but slightly lower than the frequency of the surgical laser 14.

In certain operations, the stroboscopic effect can help the operator visualize the surgical process. Where the pulsed laser energy creates a response that repeats with each laser pulse, the stroboscopic effect can slow down the appearance of the response. For example, in cataract surgery, the laser energy directed at the cataractous lens may create a bubble in the lens with each laser pulse. The bubble forms in the time period between pulses. The stroboscopic effect can show the stages of the bubble formation by illuminating a sample in time from a series of laser pulses, with each sample shifted slightly in time relative to the laser pulse. Thus, the operator can visualize the bubble formation slowed down from real time.

The stroboscopic effect can be useful for visualizing other responses as well. For example, in cataract surgery, the stroboscopic effect can be useful for visualizing fragmentation and liquefaction of the tissue, complex flow fields, occlusion of the irrigation-aspiration system, and other effects.

In addition to emitting the illuminating visible light continuously or in pulses, the illumination source 70 may emit the illuminating visible light in different intensities and colors. The illumination source 70 may be, for example, a continuous or pulsed LED or a continuous or pulsed laser diode.

The wavelength of the illuminating visible light may be selected depending upon the application. For example, for ophthalmic surgery, the ANSI standards for maximum permissible exposure and the typical retinal sensitivity of the operator should be considered. An example operating range for the wavelength of the illuminating visible light is about 570 nm to about 620 nm, for example about 590 nm. Other wavelengths within the visible spectrum may be used for the illuminating visible light.

Figure 2:
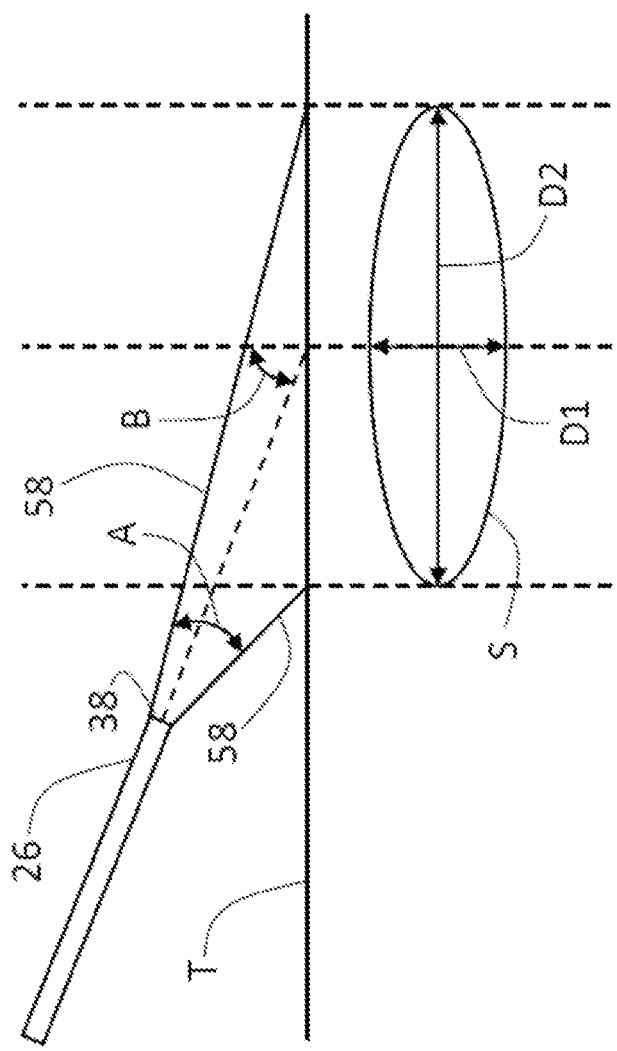
FIG. 2 shows an example illumination from a surgical laser in accordance with the disclosure.

In addition to illuminating the area of the surgical laser target and helping the operator visualize the target location and the surgical process, the illumination can also help the operator estimate the distance of the instrument tip to the boundaries of different tissue. FIG. 2 shows a schematic illustration of a tissue surface T being illuminated by illuminating visible light emitted from the distal end 38 of the output fiber-optic cable 26. The illuminating visible light exiting from the fiber tip typically has a circularly symmetric conical distribution, designated by the light cone 58 with a light cone angle A in FIG. 2. When introduced at an angle of incidence, such as the angle of incidence B in FIG. 2, such a beam forms an elliptical light spot S at the boundaries of different tissue, such as the capsule of the lens. At the tissue surface T, the spot T has a cross axis D1 and a longitudinal axis D2 as shown. The ratio of D1 to D2 is approximately equal to the cosine of the angle of incidence B. The size of D1 is proportional to the distance of the tip 38 to the tissue surface T and to the angle A of the light cone. With a known or steady light cone, the size of the spot S and the length of the cross axis D1 will get smaller as the tip 38 gets closer to the tissue surface T. By looking at the size of the cross axis D1, the operator can estimate the distance of the instrument tip 38 to the tissue surface T. The knowledge of the tip to tissue distance is important to avoid damage of critical tissues such as the capsular bag or the retina.

Figure 3:
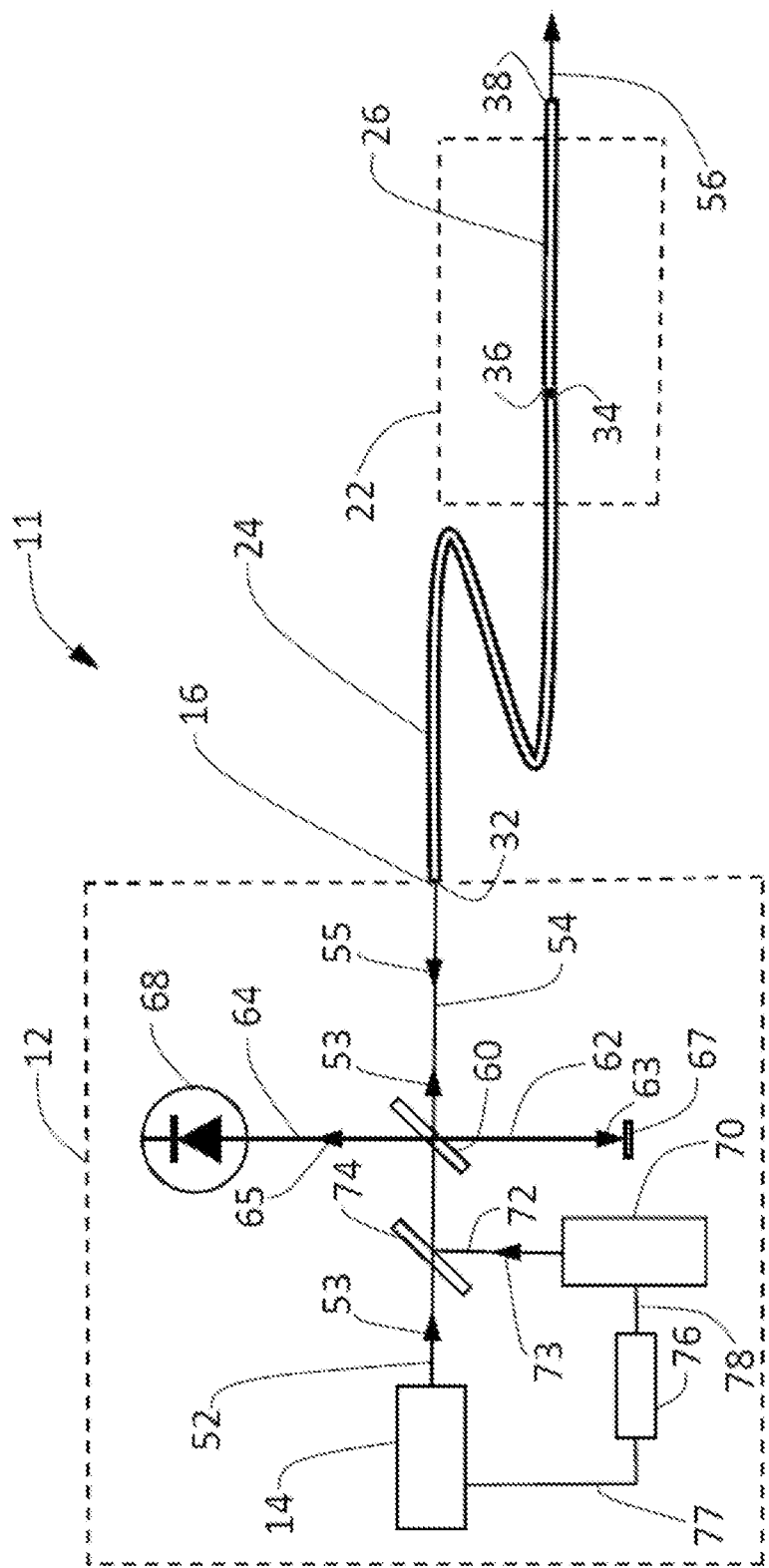
FIG. 3 shows a schematic diagram of another example laser system configured for delivering electromagnetic radiation from a surgical laser and illuminating visible light from an illumination source along with monitoring of returned electromagnetic radiation in accordance with the disclosure.

FIG. 3 shows a schematic diagram of another example laser system 11 configured for delivering electromagnetic radiation from a surgical laser and illuminating visible light from an illumination source in accordance with the disclosure. The laser system 11 is similar to laser system 10, with components and functioning as described above. In addition to the components of laser system 10, the laser system 11 further includes a return signal monitoring sensor positioned to detect returned laser electromagnetic radiation. As shown in FIG. 3, a beam splitter 60 is positioned in the optical path 54 between the laser source 14 and the output port 16 of the laser housing 12. In the illustrated embodiment, when the laser electromagnetic radiation is directed along optical path 54 in the direction of arrows 53 toward the output port 16, most or all of the laser electromagnetic radiation passes through the beam splitter 60 and continues through the output port 16 to the delivery fiber-optic cable 24 and the handpiece 22. Similarly, when the illuminating visible light is directed along optical path 54 in the direction of arrows 53 toward the output port 16, most or all of the illuminating visible light passes through the beam splitter 60 and continues through the output port 16 to the delivery fiber-optic cable 24 and the handpiece 22. A fraction, for example 1% to 10%, of the electromagnetic radiation from the laser 14 is diverted by the beam splitter 60 along optical path 64 in the direction of arrow 65 as reference signal measuring the output energy of the laser 14, designated by reference signal component 68.

As described in more detail below, depending on the conditions of use of the laser system 11, some portion of the laser electromagnetic radiation that is transmitted from the fiber-optic cable to the tissue surface T gets returned back into the fiber-optic cable in a reverse direction. The returned signal may be a combination of back-reflection, back-scattering, fluorescence, Raman scattering, etc., of the laser electromagnetic radiation. This returned electromagnetic radiation travels back through the fiber-optic cable and back along optical path 54 in the direction of arrow 55 to the beam splitter 60. The beam splitter 60 directs 1-10% of this returned laser electromagnetic radiation along optical path 62 in the direction of arrow 63. The back-reflected laser electromagnetic radiation directed along optical path 62 in the direction of arrow 63 is directed to a back-reflection monitoring sensor 67 for measuring the back-reflected laser electromagnetic radiation. The laser electromagnetic radiation returned back from the tissue can carry information about the tip-to-tissue distance, the fluorescence properties of the tissue near the tip, or other information. For example, Raman scattered light can be used to identify the molecular composition of the tissue near the fiber-optic tip.

In order to distinguish between the two principal directions of travel, the terms "forward transmission" and "forward-transmitted" are used to refer to electromagnetic radiation transmitted in a direction from the beam splitter 60 and toward the distal end 38 of the output fiber-optic cable 26, i.e., toward the distal end of the laser system 11. The term "returned" is used to refer to electromagnetic radiation that is returned from the distal end 38 of the output fiber-optic cable 26 and toward the beam splitter 60, i.e., away from the distal end of the laser system 11.

The sensor 67 may be, for example, a photodiode capable of converting the returned electromagnetic radiation into an electric signal. As one example each of components 67 and 68 may be a lead selenide photodetector. Other types of photodetectors and other types of sensors may be used. It is advantageous in certain applications to protect the detectors 67 and 68 from the illumination light by combining each of the detectors 67 and 68 with a filter absorbing the visible light.

In the example of FIG. 3, the beam splitter 60, the sensor 67, and the sensor 68 are housed within the laser housing 12. In other embodiments, one or more of these components may be located outside of the laser housing 12.

In operation of the example laser system 10 in FIG. 1 and laser system 11 in FIG. 3, the surgical laser 14 is operated to emit electromagnetic radiation, which is transmitted from the surgical laser 14 along the optical paths 52 and 54 in the direction of arrows 53 to the output port 16. In addition, the illumination source 70 is operated to emit illuminating visible light, which is transmitted from the illumination source 70 along the optical paths 72 and 54 in the direction of arrows 73 and 53 to the output port 16.

From the output port 16, the laser electromagnetic radiation and illuminating visible light enter the proximal end 32 of the delivery fiber-optic cable 24, travel through the delivery fiber-optic cable 24, and exit the delivery fiber-optic cable 24 at distal end 34. From the distal end 34 of the delivery fiber-optic cable 24, the laser electromagnetic radiation and the illuminating visible light enter the proximal end 36 of the output fiber-optic cable 26, travel through the output fiber-optic cable 26, and exit output fiber-optic cable 26 at the distal end 38 toward the target site along optical path 56. The target site may be, for example, a cataractous lens, vitreous fibers, retinal tissue, other ophthalmic tissue, or other tissue in general.

The illuminating visible light shines on the target surface, such as ophthalmic tissue, and can help the operator visualize the target location and the surgical process. The laser electromagnetic radiation may be continuous and/or pulsed, and, as described above, the illuminating visible light may be continuous and/or pulsed and may be synchronized with the surgical laser for a stroboscopic effect.

The system may comprise a computing system, e.g., a processor, memory, and software, firmware and/or hardware, that controls the surgical laser 14 and/or the illumination source 70. The computing system may also receive the signals from the monitoring sensor(s) and monitor them.

Figure 4:
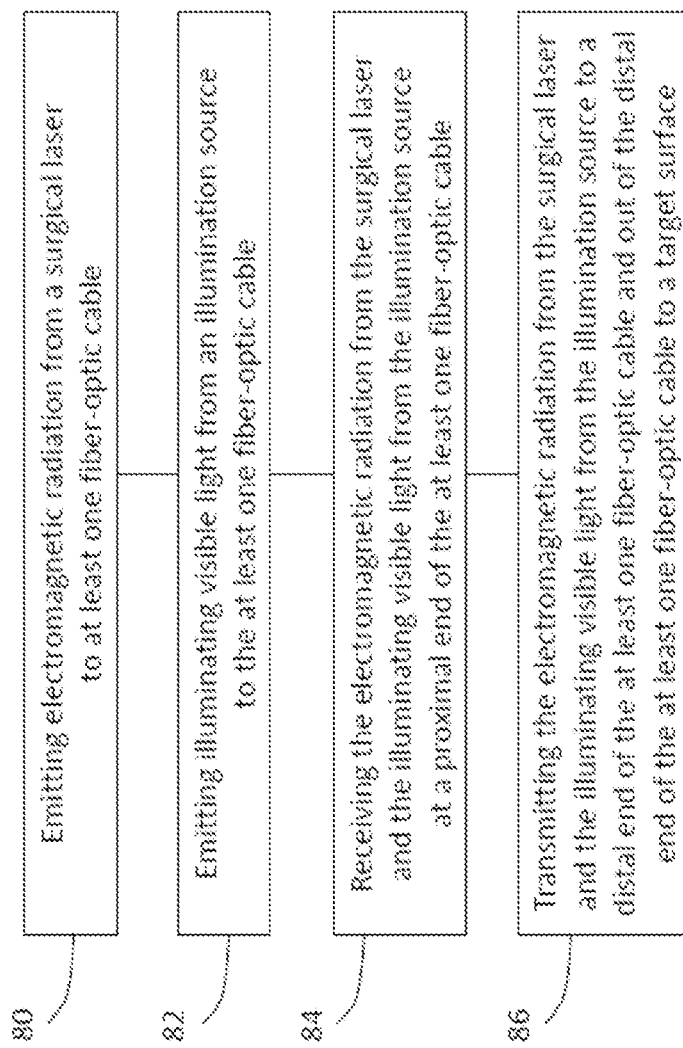
FIG. 4 shows a flow chart of an example method of operating a laser system in accordance with the disclosure.

FIG. 4 shows a flow chart of an example method of operating a laser system with illumination. The example method steps shown in FIG. 4 represent only an embodiment, as other variations are possible within the scope of the disclosure.

In step 80, electromagnetic radiation is emitted from a surgical laser to at least one fiber-optic cable. For example, electromagnetic radiation is emitted from a surgical laser 14 to the fiber-optic cables 24, 26.

In step 82, illuminating visible light is emitted from an illumination source to the at least one fiber-optic cable. For example, illuminating visible light is emitted from an illumination source 70 to the fiber-optic cables 24, 26.

In step 84, the electromagnetic radiation from the surgical laser and the illuminating visible light from the illumination source are received at a proximal end of the at least one fiber-optic cable. For example, the electromagnetic radiation from the surgical laser 14 and the illuminating visible light from the illumination source 70 are received at a proximal end 32 of the fiber-optic cable 24.

In step 86, the electromagnetic radiation from the surgical laser and the illuminating visible light from the illumination source are transmitted from the proximal end of the at least one fiber-optic cable to a distal end of the at least one fiber-optic cable and out of the distal end of the at least one fiber-optic cable to a target surface. For example, the electromagnetic radiation from the surgical laser 14 and the illuminating visible light from the illumination source 70 are transmitted from the proximal end 32 of the at least one fiber-optic cable 24, 26 to a distal end 38 of the at least one fiber-optic cable 24, 26 and out of the distal end 38 of the at least one fiber-optic cable 24, 26 to a target surface T.

As would be understood by persons of ordinary skill in the art, systems and methods as disclosed herein have advantages over prior systems and methods. For example, in some prior systems and methods, visibility near a surgical fiber tip is nonexistent or poor. With systems and methods as disclosed herein, high resolution visualization of the vicinity near the surgical fiber tip can be achieved. In addition, with stroboscopic effects and monitoring of returned signals, other visualization and monitoring advantages can be achieved. The improved visualization and monitoring can improve the surgical procedures and patient outcomes.

Persons of ordinary skill in the art will appreciate that the embodiments encompassed by the disclosure are not limited to the particular example embodiments described above. While illustrative embodiments have been shown and described, a wide range of modification, change, and substitution is contemplated in the foregoing disclosure. It is understood that such variations may be made to the foregoing without departing from the scope of the disclosure. Accordingly, it is appropriate that the appended claims be construed broadly and in a manner consistent with the disclosure.

What is claimed is:

1. A laser system comprising:
a surgical laser configured to emit electromagnetic radiation;
at least one fiber-optic cable having a proximal end and a distal end, the at least one fiber-optic cable configured to receive the electromagnetic radiation from the surgical laser at the proximal end of the at least one fiber-optic cable and to transmit the electromagnetic radiation from the surgical laser from the proximal end of the at least one fiber-optic cable to the distal end of the at least one fiber-optic cable and out of the distal end of at least one the fiber-optic cable; and
an illumination source configured to emit illuminating visible light;
wherein the at least one fiber-optic cable is configured to receive the illuminating visible light from the illumination source at the proximal end of the at least one fiber-optic cable and to transmit the illuminating visible light from the illumination source from the proximal end of the at least one fiber-optic cable to the distal end of the at least one fiber-optic cable and out of the distal end of the at least one fiber-optic cable;
wherein the illumination source is configured to emit the illuminating visible light continuously for a desired period of time.

2. A laser system comprising:
a surgical laser configured to emit electromagnetic radiation;
at least one fiber-optic cable having a proximal end and a distal end, the at least one fiber-optic cable configured to receive the electromagnetic radiation from the surgical laser at the proximal end of the at least one fiber-optic cable and to transmit the electromagnetic radiation from the surgical laser from the proximal end of the at least one fiber-optic cable to the distal end of the at least one fiber-optic cable and out of the distal end of at least one the fiber-optic cable; and
an illumination source configured to emit illuminating visible light;
wherein the at least one fiber-optic cable is configured to receive the illuminating visible light from the illumination source at the proximal end of the at least one fiber-optic cable and to transmit the illuminating visible light from the illumination source from the proximal end of the at least one fiber-optic cable to the distal end of the at least one fiber-optic cable and out of the distal end of the at least one fiber-optic cable;
wherein the illumination source is configured to emit the illuminating visible light in pulses.

3. The laser system as recited in claim 2, wherein the surgical laser is configured to emit the electromagnetic radiation from the surgical laser in pulses, and wherein the laser system is configured to synchronize the pulses from the surgical laser and the pulses from the illumination source to create a stroboscopic effect.

4. The laser system as recited in claim 1, wherein the fiber-optic cable comprises at least one optical fiber configured to receive the electromagnetic radiation from the surgical laser and the illuminating visible light from the illumination source.

5. The laser system as recited in claim 1, wherein the fiber-optic cable comprises at least a first optical fiber configured to receive the electromagnetic radiation from the surgical laser and at least a second optical fiber configured to receive the illuminating visible light from the illumination source.

6. The laser system as recited in claim 1, further comprising a beam combining component configured to combine the electromagnetic radiation from the surgical laser and the illuminating visible light from the illumination source along a common optical path.

7. The laser system as recited in claim 6, wherein the beam combining component is adapted to permit the electromagnetic radiation from the surgical laser to pass through the beam combining component to the at least one fiber-optic cable, and wherein the beam combining component is adapted to direct the illuminating visible light from the illumination source to the at least one fiber-optic cable.

8. The laser system as recited in claim 6, wherein the beam combining component is adapted to direct the electromagnetic radiation from the surgical laser to the at least one fiber-optic cable, and wherein the beam combining component is adapted to permit the illuminating visible light from the illumination source to pass through the beam combining component to the at least one fiber-optic cable.

9. A laser system comprising:
a surgical laser configured to emit electromagnetic radiation;
at least one fiber-optic cable having a proximal end and a distal end, the at least one fiber-optic cable configured to receive the electromagnetic radiation from the surgical laser at the proximal end of the at least one fiber-optic cable and to transmit the electromagnetic radiation from the surgical laser from the proximal end of the at least one fiber-optic cable to the distal end of the at least one fiber-optic cable and out of the distal end of at least one the fiber-optic cable; and
an illumination source configured to emit illuminating visible light;
wherein the at least one fiber-optic cable is configured to receive the illuminating visible light from the illumination source at the proximal end of the at least one fiber-optic cable and to transmit the illuminating visible light from the illumination source from the proximal end of the at least one fiber-optic cable to the distal end of the at least one fiber-optic cable and out of the distal end of the at least one fiber-optic cable;
wherein the at least one fiber-optic cable comprises a delivery fiber-optic cable and an output fiber-optic cable each having a proximal end and a distal end, wherein the output fiber-optic cable is positioned distal to the delivery fiber-optic cable, and wherein the proximal end of the output fiber-optic cable is configured to receive the electromagnetic radiation from the surgical laser and the illuminating visible light from the illumination source from the distal end of the delivery fiber-optic cable.

10. The laser system as recited in claim 1, further comprising a laser housing, wherein the surgical laser is located inside the laser housing, and wherein the at least one fiber-optic cable is adapted to be removably connected to the laser housing.

11. The laser system as recited in claim 1, further comprising a monitoring sensor positioned to detect returned laser electromagnetic radiation.

12. A method of operating a laser system comprising:
emitting electromagnetic radiation from a surgical laser to at least one fiber-optic cable;
emitting illuminating visible light from an illumination source to the at least one fiber-optic cable;
receiving the electromagnetic radiation from the surgical laser and the illuminating visible light from the illumination source at a proximal end of the at least one fiber-optic cable; and
transmitting the electromagnetic radiation from the surgical laser and the illuminating visible light from the illumination source from the proximal end of the at least one fiber-optic cable to a distal end of the at least one fiber-optic cable and out of the distal end of the at least one fiber-optic cable to a target surface;
wherein the step of emitting illuminating visible light from the illumination source to the at least one fiber-optic cable comprises emitting the illuminating visible light from the illumination source continuously for a desired period of time.

13. A method of operating a laser system comprising:
emitting electromagnetic radiation from a surgical laser to at least one fiber-optic cable;
emitting illuminating visible light from an illumination source to the at least one fiber-optic cable;
receiving the electromagnetic radiation from the surgical laser and the illuminating visible light from the illumination source at a proximal end of the at least one fiber-optic cable; and
transmitting the electromagnetic radiation from the surgical laser and the illuminating visible light from the illumination source from the proximal end of the at least one fiber-optic cable to a distal end of the at least one fiber-optic cable and out of the distal end of the at least one fiber-optic cable to a target surface;
wherein the step of emitting illuminating visible light from the illumination source to the at least one fiber-optic cable comprises emitting the illuminating visible light from the illumination source in pulses.

14. The method of operating a laser system as recited in claim 13, wherein the step of emitting electromagnetic radiation from a surgical laser to at least one fiber-optic cable comprises emitting the electromagnetic radiation from the surgical laser in pulses, and wherein the laser system synchronizes the pulses from the surgical laser and the pulses from the illumination source to create a stroboscopic effect.

15. The method of operating a laser system as recited in claim 14, wherein the stroboscopic effect is a slow-motion effect.

16. A method of operating a laser system comprising:
emitting electromagnetic radiation from a surgical laser to at least one fiber-optic cable;
emitting illuminating visible light from an illumination source to the at least one fiber-optic cable;
receiving the electromagnetic radiation from the surgical laser and the illuminating visible light from the illumination source at a proximal end of the at least one fiber-optic cable; and
transmitting the electromagnetic radiation from the surgical laser and the illuminating visible light from the illumination source from the proximal end of the at least one fiber-optic cable to a distal end of the at least one fiber-optic cable and out of the distal end of the at least one fiber-optic cable to a target surface;
wherein the step of emitting electromagnetic radiation from a surgical laser to at least one fiber-optic cable comprises emitting electromagnetic radiation in the mid-infrared range from the surgical laser.

17. A method of operating a laser system comprising:
emitting electromagnetic radiation from a surgical laser to at least one fiber-optic cable;
emitting illuminating visible light from an illumination source to the at least one fiber-optic cable;
receiving the electromagnetic radiation from the surgical laser and the illuminating visible light from the illumination source at a proximal end of the at least one fiber-optic cable; and
transmitting the electromagnetic radiation from the surgical laser and the illuminating visible light from the illumination source from the proximal end of the at least one fiber-optic cable to a distal end of the at least one fiber-optic cable and out of the distal end of the at least one fiber-optic cable to a target surface;
directing the electromagnetic radiation from the surgical laser from the distal end of the at least one fiber-optic cable to a cataractous lens to fragment the cataractous lens.

18. The method of operating a laser system as recited in claim 12, further comprising detecting laser electromagnetic radiation that is returned through the at least one fiber-optic cable.

\* \* \* \* \*